United States Patent [19]

Steltenkamp et al.

[11] Patent Number: 5,143,900

[45] Date of Patent: Sep. 1, 1992

[54] PERFUMES CONTAINING N-LOWER ALKYL NEOALKANAMIDE (S)

[75] Inventors: Robert J. Steltenkamp; Craig F. Eaton, both of Somerset, N.J.

[73] Assignee: Colgate-Palmolive Company, Piscataway, N.J.

[21] Appl. No.: 665,504

[22] Filed: Mar. 6, 1991

Related U.S. Application Data

[63] Continuation of Ser. No. 354,545, May 19, 1989, abandoned.

[51] Int. Cl.$^5$ .............................................. A61K 7/46
[52] U.S. Cl. ...................................... 512/26; 252/8.6; 252/174.11; 424/70; 424/84; 424/DIG. 10
[58] Field of Search .............. 512/26; 252/8.6, 174.11; 424/70, 84, DIG. 10

[56] References Cited

U.S. PATENT DOCUMENTS

| | | | |
|---|---|---|---|
| 4,301,021 | 11/1981 | Breant | 564/215 |
| 4,419,281 | 12/1983 | Breant | 512/26 |
| 4,419,282 | 12/1983 | Breant | 512/26 |

FOREIGN PATENT DOCUMENTS

| | | | |
|---|---|---|---|
| 039032 | 11/1981 | European Pat. Off. | 512/26 |
| 1421743 | 1/1976 | United Kingdom | 512/26 |

Primary Examiner—James H. Reamer
Attorney, Agent, or Firm—Bernard Lieberman; Murray M. Grill; Robert C. Sullivan

[57] ABSTRACT

Perfumes containing normal perfuming components, such as essential oils, esters, ethers, aldehydes, alcohols, hydrocarbons, ketones and lactones, have the fragrances thereof desirably altered, and often significantly strenghtened, by incorporation with them, as another perfuming component, of a N-lower alkyl neoalkanamide, such as ethyl neodecanamide, or a mixture of such neoalkanamides. It has been found that the neoalkanamides are of desirable fragrances, are stable, even in alkaline media, such as built detergent compositions, maintaining their fragrance notes in the perfumes and in perfumed products during comparatively lengthy storage periods, and are significantly substantive to surfaces contacted by them, even when such contact is made in relatively dilute media, such as aqueous wash water, as when ther neoalkanamide (preferably methyl- or ethyl neodecanamide) is a component of a perfume that has been employed to perfume a detergent composition. Furthermore, experimentation has indicated that the described neoalkanamides act to strengthen the fragrances of other perfuming components of the perfumes.

8 Claims, 4 Drawing Sheets

PERFUMES CONTAINING N-LOWER ALKYL NEOALKANAMIDE (S)

This is a continuation of application Ser. No. 07/354,545, filed May 19, 1989, now abandoned.

This invention relates to perfumes. More particularly, it relates to perfumes which contain a novel perfuming component which modifies the fragrance of the perfume, is substantive to surfaces to which the perfume is applied, is satisfactorily stable on storage and in contact with alkaline media, and increases the strengths of aromas of various other perfuming components.

The perfuming art is an ancient one, and for thousands of years it has been known how to make a wide variety of delightful perfumes from mixtures of natural perfuming materials. Usually such perfumes were blends of essential oils obtained from flowers, fruits, leaves, roots or woody portions of various plants, a fixative, such as musk, civet, castoreum, ambergris, or gum benzoin, and a solvent, such as alcohol. Many fine perfumes contained a multiplicity of ingredients, usually at least ten, blended together to produce unique and lasting fragrances.

Although natural substances are still used in expensive perfumes, increasing costs, and inconsistencies in their fragrances due to differences in source materials, together with advancements in synthetic chemistry, have led to the replacements of most natural perfume ingredients by synthetics. However, perfumes are still usually complex blends of the same types of chemical compounds as were found in the natural sources, including esters, aldehydes, alcohols, hydrocarbons, lactones, ketones, ethers and essential oils, frequently with a synthetic fixative. Perfumery chemists are continuing to search for and to synthesize new perfumery materials, especially those which will contribute desirable fragrances to their products, and those which will strengthen the fragrance of a perfume and make it more substantive and longer lasting. As an outcome of such searching it has been found by the present inventors that certain neoalkanamides (trialkyl acetamides) can be useful components of perfumes, adding their specific characteristic fragrances, and strengthening the perfume and the fragrance emitted by it. It is considered highly unusual for an amide to have desirable fragrance characteristics. Additionally, the present amides have been found to be substantive to surfaces contacted by such perfumes and are of satisfactory stability on storage and in the presence of alkaline media. A further advantage of the present perfumes containing these neoalkanamides is that although their fragrances are pleasant to the human olfactory sense, they serve as repellents to insects, which repellent activity is described in U.S. patent application Ser. No. 06/894,985 now abandoned, entitled N-Alkyl Neoalkanamide now abandoned Insect Repellents, which was filed on the same day as Ser. No. 06/894,983, the grandfather of the present application, by Robert J. Steltenkamp (one of the present co-inventors), which application is hereby incorporated herein by reference. When the present perfumes are employed to perfume any of various household products, such as detergents and surface treating compositions (waxes and polishes), materials washed and surfaces treated with them have neoalkanamide deposited on and held to them, and thereby become aromatic and insect repellent.

In accordance with the present invention a novel liquid perfume, suitable for perfuming soaps and detergent compositions, comprises a N-lower alkyl neoalkanamide or a mixture of a plurality of such N-lower alkyl neoalkanamides, wherein the lower alkyl is of 1 to 4 carbon atoms and the neoalkanoyl moiety thereof is of 5 to 14 carbon atoms, and at least one and preferably a plurality of perfume component(s) of type selected from the group consisting of essential oils, esters, ethers aldehydes, alcohols, hydrocarbons, ketones and lactones, in which the content of such neoalkanamide(s) is from 0.1 to 98%. Also within the invention are various household products that have been perfumed with the described perfume. Such products include built and unbuilt soap and synthetic organic detergent compositions, in particulate, liquid, gel, paste, bar or cake, and other acceptable forms, hard surface cleaning detergent compositions, hair shampoos, rug and upholstery shampoos, floor polishes and waxes, furniture polishes and waxes, and shelving papers. Also within the invention are insect repellents and insecticides perfumed with the present perfumes, and synthetic organic polymeric "plastic" products containing a perfume of the invention, such as pet care articles, e.g., food dishes, bed frames, grooming aids, of perfumed plastic, and of other materials.

Searches of the prior art have not resulted in the finding of any disclosure of any N-lower alkyl neoalkanamide. In U.S. patent application Ser. No. 716,871 (Steltenkamp and Camara), filed Mar. 27, 1985 now U.S. Pat. No. 4,692,982, N-higher alkyl neoalkanamides are disclosed and in U.S. patent application Ser. No. 894,985, now abandoned, (Steltenkamp), entitled N-alkyl Neoalkanamide Insect Repellents, filed on the same day as the present application, N-lower alkyl neoalkanamides are disclosed to be new compounds. However, present applicants, while not claiming to be the inventors of N-lower alkyl neoalkanamides, are the inventors of perfumes containing such compounds.

The N-lower alkyl neoalkanamides utilized in this invention include those wherein the alkyl is of 1 to 4 carbon atoms, preferably one or two carbon atoms (methyl or ethyl), and sometimes more preferably, ethyl. The neoalkanoyl moiety, which may be derived from any of the suitable neoalkanoic acids, various of which are available commercially, will normally be of 5 to 14 carbon atoms (of a number of carbon atoms in the range of 5 to 14), preferably 7 to 12 carbon atoms and more preferably of 9 to 11 carbon atoms, such as neodecanoyl. Among the available neoalkanoic acids, from which the amides can be made, are neopentanoic acid, neoheptanoic acid, neononanoic acid, neodecanoic acid, neododecanoic acid, neotridecanoic acid, and neotetradecanoic acid. Usually the alkyl groups of the amides are straight chain but they can also branch. Pure neoalkanamides of the types described may be made but often the commercial or technical grade acids, which may be used, and the amides made from them, will be mixtures.

The present operative N-lower alkyl neoalkanamides are of the formula wherein R, R' and R" are alkyl groups, the sum of the carbon atom contents of which is in the range of 3 to 12, and R''' is a lower alkyl group, normally of 1 to 4 carbon atoms. Further details with respect to R, R' and R" will be given later, in conjunction with a description of neoalkanoic acids which may be employed as starting materials for the production of the neoalkanamides.

Infrared absorption spectra for some representative and preferred N-lower alkyl neoalkanamides utilized in this invention are shown in the drawing, in which.

Figure 1:
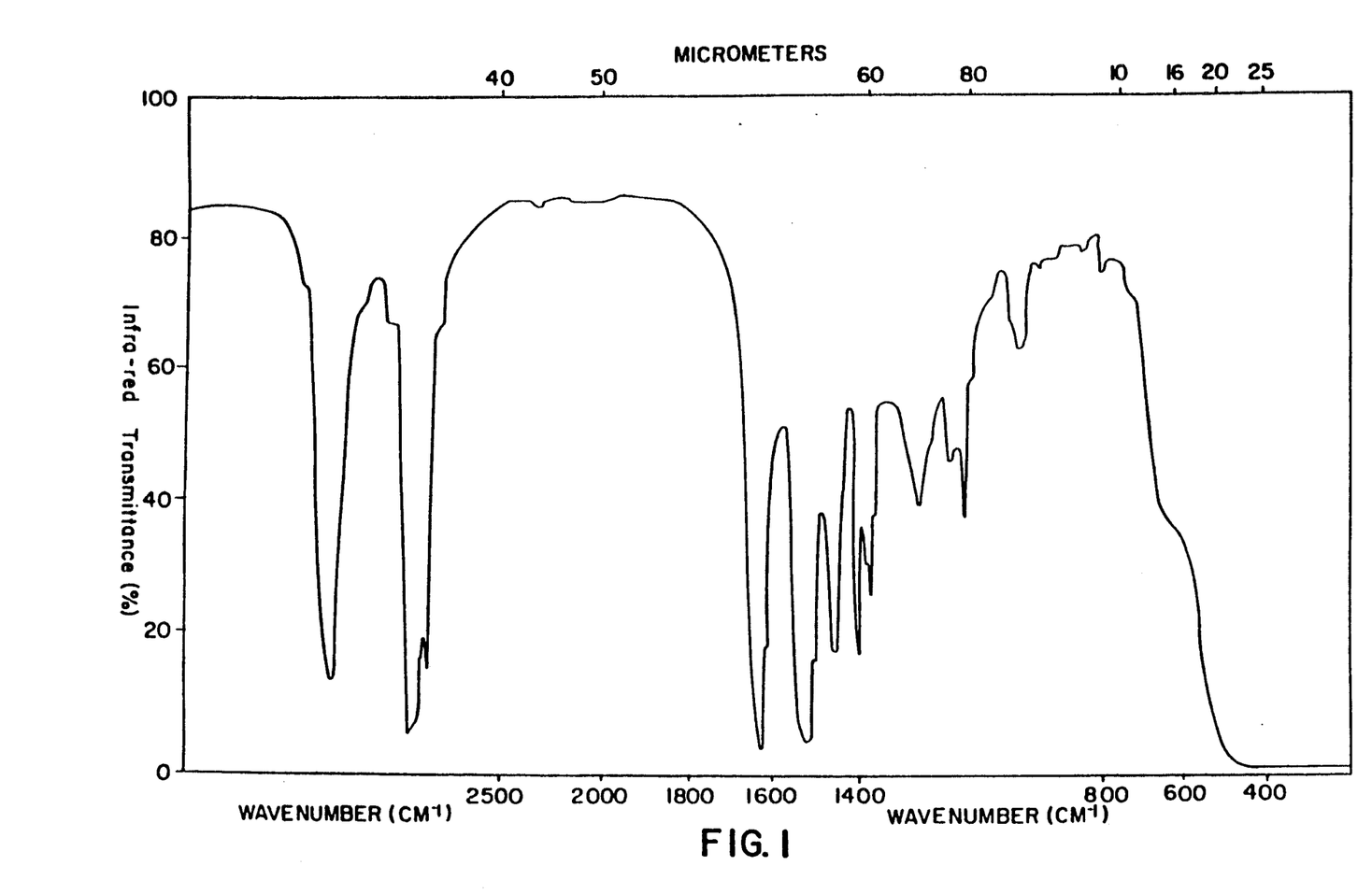
FIG. 1 is an infrared absorption spectrograph of a sample of methyl neodecanamide.
Figure 2:
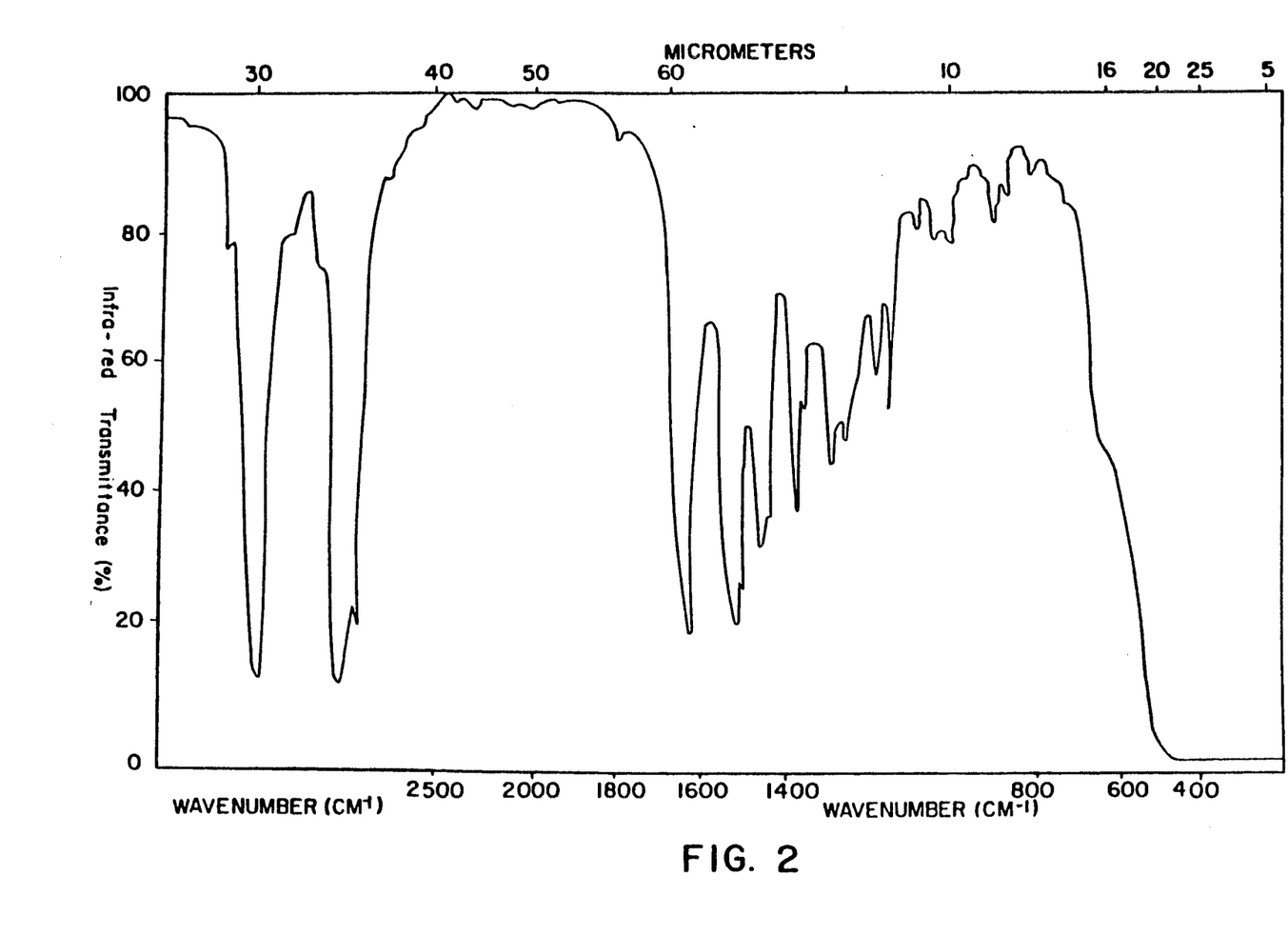
FIG. 2 is an infrared spectrograph of a sample of ethyl neodecanamide.
Figure 3:
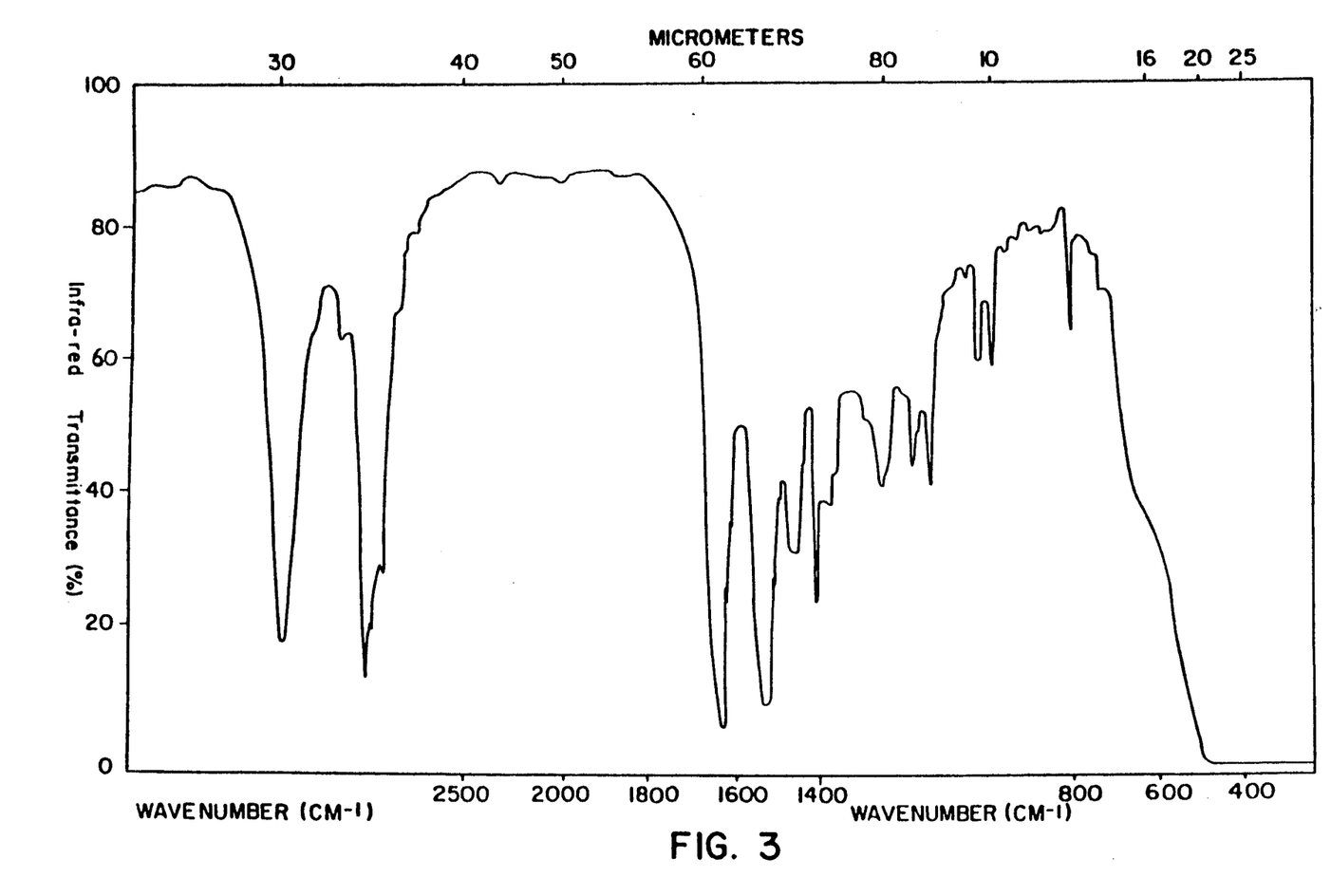
FIG. 3 is an infrared spectrograph of a sample of methyl neoheptanamide.
Figure 4:
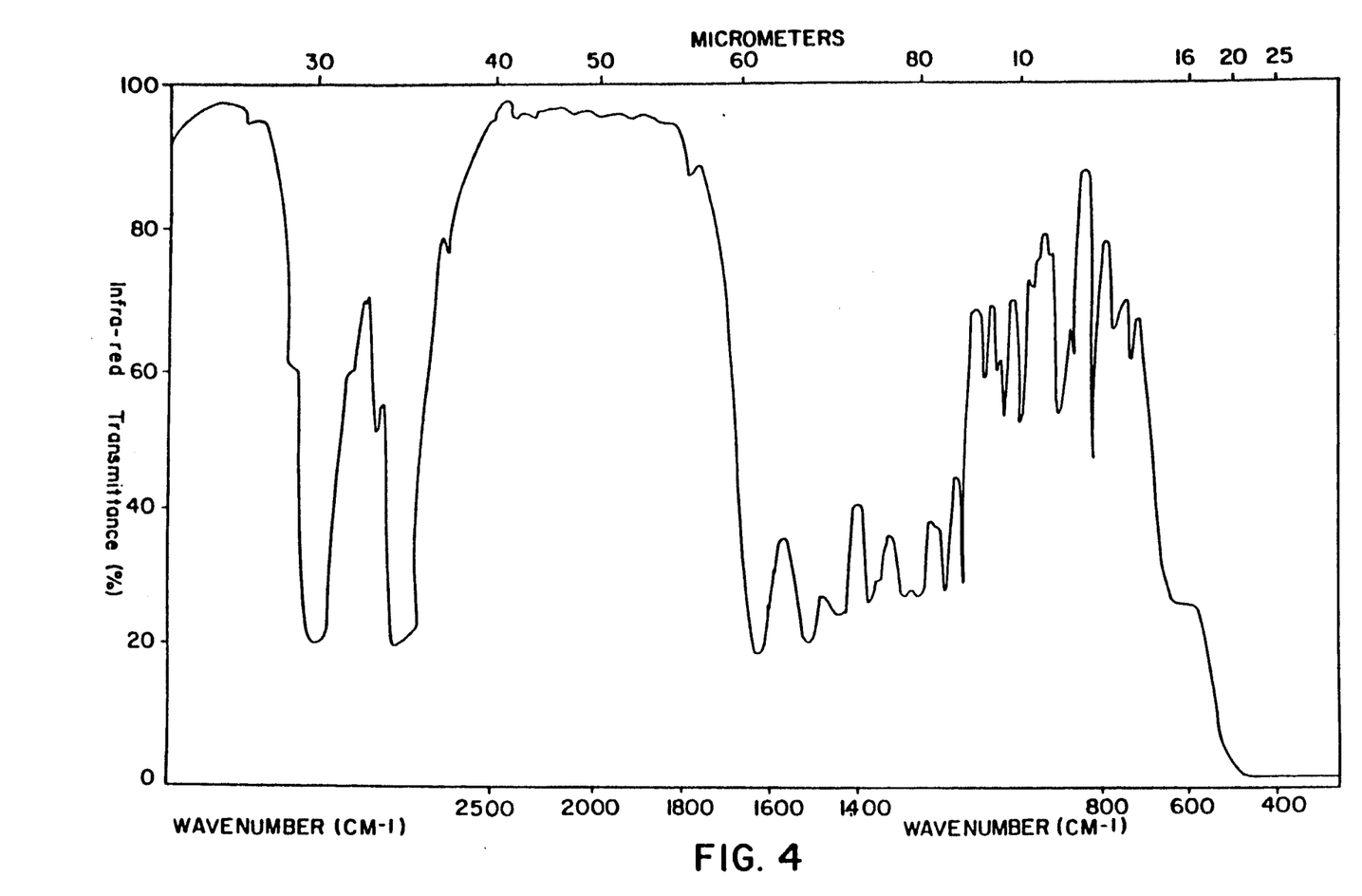
FIG. 4 is an infrared spectrograph of a sample of ethyl neoheptanamide.

To make the neoalkanamides employed in this invention neoalkanoyl chloride reactant is slowly reacted with the appropriate primary amine, in ethyl ether, after which reaction the reaction mixture is washed with distilled water, dilute hydrochloric acid solution, dilute sodium hydroxide solution, and more distilled water, until it is neutral to pH paper. The ether is then removed by means of a steam bath, followed by employment of a vacuum evaporator. The reaction product obtained is water white to light amber in color and is essentially pure. In an alternative method, the neoalkanoic acid may be reacted directly with the lower alkylamine.

Neoalkanoic acids, such as neodecanoic acid, neoheptanoic acid and neopentanoic acid, are available from Exxon Chemical Americas, which synthesizes them by reacting a suitable branched alkene and carbon monoxide under high pressure at elevated temperature in the presence of aqueous acidic catalyst (Koch reaction). The general mechanism involved includes generation of carbonium ion, followed by complexation with carbon monoxide and the catalyst to form a "complex", which is subsequently hydrolyzed to generate free acid. The formula of the free acid is In neodecanoic acid, for example, the total number of carbon atoms in R, R' and R" is 8, 31% of the neodecanoic acid is of a structure wherein R' and R" are both methyl and R is hexyl, 67% is of a formula wherein R' is methyl, R" is alkyl of a carbon atoms content greater than that of methyl and less than that of R' and R is of a carbon atoms content less than that of hexyl and greater than that of R"; and 2% is of the formula wherein R' and R" are both of a carbon atoms content greater than that of methyl and less than that of R, and R is of a carbon atoms content less than that of hexyl and greater than those of R' and R". Among other neoalkanoic acids that are available and useful to make the present amides may be mentioned others in the 7 to 16 carbon atoms content range, such as neoheptanoic, neononanoic, neodecanoic, neododecanoic, neotridecanoic and neotetradecanoic acids. In the various neoalkanoic acids mentioned, when R is alkyl of five or more carbon atoms such alkyl is branched. The acyl chloride starting materials for the reactions to produce the N-lower alkyl neoalkanamides may be made from the neoalkanoic acids and suitable chlorinating agents, such as phosphorus trichloride, and are available from the Lucidol Division of Pennwalt, Inc.

The described N-lower alkyl neoalkanamides are normally liquids and are of sufficient volatilities and lasting effects to be effective perfume materials. They are of pleasing aromas and are relatively long lasting. Additionally, they interact with other perfume components and often strengthen and otherwise improve the aromas of such components in the total perfume. A preferred neoalkanamide, N-ethyl neodecanamide, is of a mild, somewhat rose-like fragrance, with a slight plum or apple fruitiness. The fragrance of a drop, on a perfumer's blotter strip, is still noticeable after two weeks. N-methyl neodecanamide possesses a light, fresh, fruity pear-like aroma with floral undertones. Its fragrance is also still detectable after two weeks. N-ethyl neoheptanamide has a "green", fruity, wine-like odor, which lasts one or two days, and N-methyl neoheptanamide has a fresh, clean, camphor-type odor, which also lasts one or two days. Other N-lower alkyl neoalkanamides of the class described herein are also aromatic and persistent, and tend to be substantive to surfaces to which they are applied. Additionally, they are generally of satisfactory stabilities in a wide variety of preparations, even those which may be of substantial alkalinities.

With the N-lower alkyl neoalkanamide(s) component(s) of the present perfumes there may be employed any of the various well-known aromatic perfuming components, fixatives, solvents, extenders, stabilizers and adjuvants. Of these the primarily perfuming materials will often fall in one or more of the following classes: essential oils, esters, ethers, aldehydes, alcohols, hydrocarbons, ketones, and lactones, but various other classes of materials may also be present, such as pyrrones, and pyrroles.

Among preferred components of rose, lily, tropical fruit and floral-woody-amber type perfumes are the following: essential oils - citrus, evergreen, jasmine, lily, rose, ylang ylang; esters - phenoxyethyl isobutyrate, benzyl acetate, p-tertiary butyl cyclohexyl acetate, guaiacwood acetate, linalyl acetate, dimethylbenzyl carbinyl acetate, phenylethyl acetate, linalyl benzoate, benzyl formate, ethymethylphenyl glycidate, allylcyclohexane propionate, styrallyl propionate, and benzyl salicylate; ethers benzylethyl ether; aldehydes - alkyl aldehydes of 8 to 18 carbon atoms, bourgeonal, citral, citronellal, citronellyl oxyacetaldehyde, cyclamen aldehyde, hydroxy citronellal, and lilial; alcohols - anethol, citronellol, eugenol, geraniol, linalool, phenylethyl alcohol and terpineol; hydrocarbons balsams and terpenes; ketones - ionones, alpha-isomethyl ionone, and methylcedryl ketone; lactones - gamma-alkyl lactone wherein the alkyl is of 8 to 14 carbon atoms; pyrrones hydroxy lower alkyl pyrrone wherein the alkyl is of 1 to 4 carbon atoms; and pyrroles - benzopyrrole.

Although the components mentioned above are preferred in perfumes of the invention for producing the types of fragrances previously mentioned, various other perfumery materials may also be employed, including lemon oil, lime oil, orange oil, bergamot oil, sweet orange oil, petitgrain bigarade oil, rosemary oil, dimethyl anthranilate, indole, methyl anthranilate, jasmine oil, patchouly oil, vetiver bourbon oil, vanillin, ethyl vanillin, coumarin, 3-methyl nonan-3-yl-acetate, methyl ionone, synthetic lily of the valley oil, synthetic red rose oil, 3-methyl nonan-3-ol, alpha-amyl cinnamic aldehyde, methyl salicylate, amyl salicylate, lavandin, isobutyl heptenone, cedryl acetate, ethyl linalyl acetate, neryl acetate, nerol, d-limonene, cuminic aldehyde, linalyl propionate, nerolidyl acetate, nerolidyl formate, alpha-pinene, isobutyl linalool, methylnaphthyl ketone, linalyl isobutyrate, paracresyl caprylate, paracresyl phenylacetate, sandalwood oil, coriander oil, sassafras oil, cassia oil, angelica root oil, Peruvian balsam, clove oil, mace oil, menthol, and almond oil.

In addition to the named fragrance components there may also be employed fixative type materials, including musk, civet, castoreum, ambergris, gum benzoin, musk ambrette, musk ketone, musk xylol, oleoresin orris root, resinoid benzoin Siam and resinoid opopanax, as well as various other resins, gums, synthetic musks and other fixatives. Also components of perfumes are alcohols and other suitable solvents and media, as well as preservatives, antioxidants, stabilizers and viscosity and volatility modifiers.

The perfumes and perfuming materials of this invention may contain from 0.1 to 98% of N-lower alkyl neoalkanamide(s), with the balance thereof being other fragrance materials and perfume constituents, which may include solvents, liquid media and/or particulate or powder bases, such as wood particles, sachet materials and clays. Preferably the perfume will be in liquid state, more preferably in a lower alcoholic solvent, e.g., ethanol, and the concentration of N-lower alkyl neoalkanamide therein will be in the range of 1 to 60%. More preferably, such concentration will be in the range of 2 to 30% and most preferably it will usually be in the range of 5 to 15%, e.g., 10%. Normally, the proportion of fixative(s) will be less than that of the fragrance material, and will usually be in the range of 0.1 to 5%. The proportion of solvent may be variable but will usually be from 20 to 95%, preferably 50 to 90%, and may be omitted entirely from some perfumes which are to be employed as concentrates, as when the perfume is added to a product or composition, rather than being a handkerchief perfume.

Although the proportions of the various non-N-methyl neoalkanamide fragrance components of the perfume are variable, with individual components ranging from 0.01 to 30% in some cases, and sometimes with certain of the classes of such materials being omitted from the formulas, normally there will be present in most perfume formulas at least one ester, at least one aldehyde and at least one alcohol representative of the fragrance classes. The proportions cf each of such classes will usually be at least 1%, with at least one of such classes being present to the extent of at least 5% and sometimes at least 10%. However, in other instances one or more of the three mentioned classes of fragrance components may be omitted, as in preferred floral-woody-amber perfumes which may comprise from 5 to 40% of citrenellol, 5 to 30% of geraniol and 2 to 40% of phenylethyl alcohol, with such proportions preferably being in the ranges of 5 to 20%, 5 to 25% and 2 to 15%, e.g., 8%, 10%, and 5%, respectively. The total of non-N-methyl neoalkanamide fragrance components present in the invented perfumes will usually be in the range of 5 to 99%, preferably 50 to 90%, with the greater percentages being present in the concentrates (from which solvent is omitted).

The proportion of perfume (usually as non-solvent concentrate) employed in various household and other products of this invention will usually be from 0.1 to 10%, preferably 0.5 to 5% and frequently 1 to 3%, with the content of N-lower alkyl neoalkanamide normally being within the range of 0.01 to 5%, preferably 0.1 to 2% and often 0.2 to 1%. However, in perfuming, odorant or air freshening sprays the range of concentrations of perfume may be increased to 5 to 25% and even to as high as 50%, and sometimes the perfume concentrate may be employed undiluted.

The invented perfumes may be usefully employed in a wide variety of household products and in various other compositions and articles. Representative of these are detergent compositions of various types, insect repellents, insecticides, paper items, textiles, surface treating compositions and synthetic organic polymeric "plastic" articles. The detergent compositions include built and unbuilt particulate, liquid, gel, paste and bar or cake detergents, such as are employed as laundry detergents, rug shampoos, human hair shampoos, upholstery cleaners, and hard surface cleaners (including scouring cleansers and wall and floor cleaners). The insect repellent compositions may be in liquid, gel, paste, powder or other suitable form, as may be insecticides perfumed with the present compositions, although the insecticides will normally be in liquid solvent or liquefied gas solution or emulsion.

Detergent compositions for washing hard or soft surfaces will comprise a detersive proportion of soap or synthetic organic detergent and a perfuming proportion of the invented perfume. For built particulate laundry detergent compositions there will normally be employed 1 to 35% of one or more synthetic organic detergents selected from the broad class or group consisting of anionic, nonionic, amphoteric, ampholytic and zwitterionic detergents, and mixtures thereof, 10 to 90% builder(s) for such detergent(s), and 0.1 to 10% of an invented perfume, preferably 7 to 30% of a synthetic organic detergent selected from the narrower class or group consisting of anionic and nonionic detergents, and mixtures thereof, 20 to 75% of water soluble and/or or water insoluble builder salt(s) for such detergent(s), 0 to 50% of water soluble filler salt, and 0.5 to 5% of an invented perfume. Liquid detergent compositions will usually comprise 2 to 25% of synthetic organic detergent selected from the broad group, and mixtures thereof, 5 to 40% of builder(s) for such detergent(s) 40 to 90% of a liquid medium for the detergent and builder, usually an aqueous medium, and 0.1 to 10% of described perfume, preferably being of 3 to 20% of synthetic organic detergent of the narrower group, or a mixture thereof, 10 to 30% of water soluble and/or water insoluble builder salts for such detergent(s), 0 to 20% of water soluble filler salt, 50 to 90% of water, and 0.5 to 5% of invented perfume. Shampoos will normally comprise from 2 to 25% of one or more of the described broad group of synthetic organic detergents in an aqueous medium and preferably will be of 5 to 22% of the narrower group, 0 to 20% of water soluble filler salt, 50 to 90% of water and 0.1 to 10% of invented perfume. Rug shampoos will usually include 1 to 35% of one or more of the described detergents (which may be water soluble soaps), 0 to 40% of builder(s) for the detergent, and 0.1 to 10% of invented perfume, in a liquid medium. Detergent bars may be of sodium higher fatty acid soap or of the described broad group of detergents, and will include 0.1 to 10% of invented perfume. Paper items, such as packaging, boxes, stationery, facial tissues and wallpaper, may be treated with the present perfumes by being sprayed onto surfaces thereof during manufacture or after manufacture, and similarly, plastic articles, such as pet care articles (which may also be made of other materials) may be treated with the invented perfumes during or after manufacture. The perfumes are also useful in various cosmetics, such as skin lotions, skin tanning preparations, sun screens, hair dressings and hair conditioners. The percentage of perfumes in such products will usually be within the ranges given previously.

The following examples illustrate the invention but do not limit it. Unless otherwise specified, all parts and percentages are by weight and all temperatures are in °C.

EXAMPLE 1

| Component | Percent |
| --- | --- |
| p-Tertiary butyl cyclohexyl acetate | 12.0 |
| N-ethyl neodecanamide | 10.0 |
| Linalool | 10.0 |
| Geraniol | 10.0 |
| Benzyl salicylate | 10.0 |
| Benzyl acetate | 10.0 |
| Citronellol | 8.0 |
| Terpineol | 8.0 |
| alpha-Isomethyl ionone | 6.0 |
| Linalyl acetate | 5.0 |
| Phenylethyl alcohol | 5.0 |
| Methylcedryl ketone | 3.0 |
| Ionone (alpha/beta) | 1.0 |
| Hydroxycitronellal-methyl anthranilate Schiff base | 1.0 |
| Ambreine compound (CFE No. 2 [Colgate]) | 1.0 |
| | 100.0 |

The components are blended together in a conventional mixer and the resulting perfume compound is characterized as woody-floral-amber. In it the neodecanamide has a harmonizing effect and increases depth of odor. It also appears to strengthen the perfume and make it more persistent. Similar good effects are obtainable by substituting N-methyl neodecanamide for the ethyl homologue or by employing others of the described N-lower alkyl neoalkanamides in place thereof, or by using mixtures of such materials. Specifically, the N-methyl neodecanamide harmonizes and floralizes the accord between the other perfume components and strengthens the fragrance.

EXAMPLE 2

| Component | Percent |
| --- | --- |
| Styrallyl propionate | 20.0 |
| N-ethyl neodecanamide | 15.0 |
| gamma-Undecalactone | 10.0 |
| Anethol | 10.0 |
| Benzyl acetate | 10.0 |
| Ethylmethylphenyl glycidate | 5.0 |
| Benzyl formate | 5.0 |
| Dimetol (Givaudan) | 5.0 |
| Hydroxyethyl pyrrone (1% in diethyl phthalate) | 5.0 |
| Allylcyclohexane propionate | 5.0 |
| gamma-Nonalactone | 5.0 |
| Linalyl benzoate | 4.0 |
| Ylang ylang extra | 1.0 |
| | 100.0 |

The components are mixed together to make a tropical fruit fragrance, suitable for use in household products, such as detergent compositions, soaps and in cosmetics. The N-ethyl neodecanamide strengthens the fragrance and improves substantivity and persistence, while also making the accord more natural, juicier and less lactonic. Instead of the n-ethyl neodecanamide there may be substituted in the above perfume formula other N-lower alkyl neoalkanamides, such as N-methyl neodecanamide, N-ethyl neoundecanamide, N-ethyl neononanamide, N-n-propyl neoheptanamide, amd N-isopropyl neotetradecanamide. While each of the mentioned neoalkanamides has a different fragrance and all are of different stabilities, substantivities, persistences and fragrances, all are suitable for use in perfumes and contribute their properties to the final fragrances of the perfume compounds or handkerchief perfumes, which may be produced by dissolving in 5 parts of ethanol.

EXAMPLE 3

| Component | Percent |
| --- | --- |
| Citronellol | 25.0 |
| Phenylethyl alcohol | 25.0 |
| N-ethyl neodecanamide | 10.0 |
| Geraniol | 10.0 |
| Phenoxyethyl isobutyrate | 3.9 |
| Linalool | 3.0 |
| p-Tertiary butylcyclohexyl acetate | 3.0 |
| Geranyl acetate | 2.0 |
| Eugenol | 2.0 |
| Phenylethyl acetate | 2.0 |
| Benzyl acetate | 2.0 |
| alpha/beta Ionone | 2.0 |
| Lauric aldehyde (10% solution in diethyl phthalate) | 2.0 |
| alpha-Isomethyl ionone | 2.0 |
| Dimethylbenzyl carbinyl acetate | 1.0 |
| Guaiacwood acetate | 1.0 |
| Rose oxide R (10% solution in diethyl phthalate) | 1.0 |
| Ylang ylang (complete) | 1.0 |
| Undecylenic aldehyde (10% in diethyl phthalate) | 1.0 |
| Damascenone (Firmenich, [1% solution in diethyl phthalate]) | 1.0 |
| Citral | 0.1 |
| | 100.0 |

The above components are mixed together to form a perfume compound which is of a rose fragrance. In the perfume the N-ethyl neodecanamide causes the fruity ester aspect of the rose fragrance to take on a sugary, jam-like quality, while the ionones are subdued. Additionally, the perfume is strengthened and its substantivity and persistence are increased.

EXAMPLE 4

| Component | Percent |
| --- | --- |
| Hydroxycitronellal (synthetic) | 28.0 |
| N-methyl neodecanamide | 20.0 |
| Cyclamen aldehyde | 1.0 |
| Geraniol | 20.0 |
| Citronellol | 15.0 |
| Brahmanol 10 (Dragoco) | 5.0 |
| Phenylethyl alcohol | 3.0 |
| Heliotropine | 2.0 |
| Indole (10% solution in diethyl phthalate) | 2.0 |
| alpha/beta Ionone | 1.0 |
| gamma Nonalactone | 1.0 |
| Lilial (Givaudan) | 1.0 |
| Citronellyl oxyacetaldehyde | 0.5 |
| Bourgeonal (Naarden) | 0.5 |
| | 100.0 |

The perfume compound of the above formula is made by mixing of the components, and the result is a lily fragrance. The presence of the N-methyl neodecanamide sweetens and naturalizes the accord, particularly the drydown, and appears to strengthen the perfume and increase its substantivity to substrates, as well as its persistence after application or use. The perfume compound, when incorporated in household products, such as detergents, cleansers, polishes and shampoos, is fragrant, substantive, persistent and stable, and additionally possesses insect repellent properties, which are often desirable, especially in rug shampoos, floor and wall cleaners, cosmetic lotions and odorants.

Other N-lower alkyl neoalkanamides, when substituted for the N-methyl neodecanamide, such as N-ethyl neodecanamide, N-butyl neooctanamide, and N-methyl neotridecanamide, will have similar effects.

EXAMPLE 5

| Component | Percent |
|---|---|
| Sodium linear tridecyl benzene sulfonate | 20.0 |
| Sodium tripolyphosphate | 37.0 |
| Sodium carbonate | 10.0 |
| Sodium bicarbonate | 10.0 |
| Borax | 5.0 |
| Enzyme blend (proteolytic + amylolytic in powdered carrier) | 1.0 |
| Sodium carboxymethylcellulose | 0.5 |
| Fluorescent brightener | 1.0 |
| Perfume (of Example 1 formula) | 5.0 |
| Water | 10.5 |
| | 100.0 |

All of the components of this built particulate detergent composition except the enzyme powder and perfume are mixed together in an aqueous slurry, which is spray dried to hollow globular bead form, of particle sizes in the range of No's. 10 to 100, U.S. Sieve Series. Subsequently, the enzyme powder is blended with the spray dried beads and the perfume, in liquid state, is sprayed onto the mixture, while it is being tumbled, to form a uniform composition.

EXAMPLE 6

Scouring Cleanser

| Component | Percent |
|---|---|
| Silex (finely divided silica powder) | 96.0 |
| Sodium linear dodecyl benzene sulfonate | 2.0 |
| Perfume (of Example 1 formula) | 2.0 |
| | 100.0 |

EXAMPLE 7

Built Liquid All-Purpose Detergent

| Component | Percent |
|---|---|
| *Nonionic Detergent | 1.0 |
| Sodium linear dodecyl benzene sulfonate | 2.0 |
| Sodium cumene sulfonate | 5.0 |
| Sodium carbonate | 5.0 |
| Sodium bicarbonate | 1.0 |
| Fluorescent brightener | 0.02 |
| Dye | 0.01 |
| Perfume (of Example 1 formula) | 1.5 |
| Water (deionized) | 84.47 |
| | 100.0 |

*Condensation product of 1 mole of higher fatty alcohol mixture averaging 10 carbon atoms, with 5 moles of ethylene oxide.

EXAMPLE 8

Carpet Cleaner

| Component | Percent |
|---|---|
| Sodium salt of lauric monoethanolamide sulfosuccinate | 29.5 |
| Mixed lipolytic, proteolytic and amylolytic enzymes | 2.0 |
| Sodium tripolyphosphate | 20.0 |
| Sodium hexametaphosphate | 5.0 |
| Sodium monophosphate | 3.5 |
| Sodium bicarbonate | 20.0 |
| Urea | 8.0 |
| *Micro-Cel ® | 10.0 |
| Perfume (of Example 2 formula) | 2.0 |
| | 100.0 |

*Finely divided hydrated synthetic calcium silicate (Johns-Manville Products Corp.)

This product should be diluted 1:30 with water before use. One hundred grams will suffice to clean about ten square meters of soiled carpeting.

EXAMPLE 9

Upholstery Cleaner

| Component | Percent |
|---|---|
| *Sulframin OBS | 10.0 |
| Aqueous ammonia (28%) | 30.0 |
| Water | 58.0 |
| Perfume (of Example 2 formula) | 2.0 |
| | 100.0 |

*Linear alkylaryl sulfonic acid (Witco Chemical Corp.)

Before use this upholstery cleaner is mixed 1:3 by volume with Stoddard solvent.

EXAMPLE 10

Hair Shampoo

| Component | Percent |
|---|---|
| Ammonium monoglyceride sulfate | 22.0 |
| Hydroxypropyl methyl cellulose | 1.0 |
| Polyacrylamide | 1.0 |
| Perfume (of Example 3 formula) | 1.2 |
| Deionized water | 74.8 |
| | 100.0 |

EXAMPLE 11

Skin Cream

| Component | Amount (as indicated) |
|---|---|
| Yellow ceresin wax | 2.0 ounces |
| Yellow beeswax | 2.0 ounces |
| Stearic acid | 2.0 ounces |
| White petrolatum | 4.0 ounces |
| White mineral oil | 8.0 fluid ounces |
| Water | 6.0 fluid ounces |
| Borax | 0.3 ounce |
| Triethanolamine | 0.5 fluid ounce |

The ceresin, beeswax, petrolatum, stearic acid and white mineral oil are melted together by heating to 71° C. The borax is dissolved in hot water and the triethanolamine is added to the solution, with the temperature being raised to 71° C. The aqueous solution is poured into the melted wax mixture, with stirring, and stirring is continued as the mixture is removed from the heat. When it begins to thicken there are added to it 14 grams of perfume of the formula of Example 4.

EXAMPLE 12

Body Lotion

| Component | Parts |
|---|---|
| Glyceryl monostearate | 50.0 |
| Oleic acid | 30.0 |
| Mineral oil | 15.0 |
| Lanolin | 10.0 |
| Triethanolamine | 12.0 |
| Sodium lauryl sulfate | 10.0 |
| Preservative | 10.0 |
| Water (deionized) | 980.0 |
| Perfume (of formula of Example 3) | 15.0 |
| | 100.0 |

EXAMPLE 13

Bar Soap

| Component | Percent |
|---|---|
| *Higher fatty acid soap | 88.0 |
| Perfume (of formula of Example 4) | 1.5 |
| Titanium dioxide | 1.0 |
| Preservative (stannic chloride) | 0.2 |
| Water | 9.3 |
| | 100.0 |

*80:20 tallow:coco sodium soap

Instead of soap bars and cakes, soap-synthetic bars can be made by substituting sodium coco-monoglyceride sulfate for up to 25% of the soap content of the formula. Similarly, by employing a suitable plasticizer all-synthetic detergent bars can be made.

Preservative, titanium dioxide, perfume and some water are milled with the dried soap chips (which contain about 8% water) and are plodded to bar form, after which the bars are cut to lengths and pressed to cake shape. Laundry bars can be made by adding 20 to 40% of builder salt, such as sodium tripolyphosphate and/or sodium carbonate to the formula, usually with an increase in the moisture content to improve plasticity during processing. Framed laundry bars and synthetic laundry bars can also be made, and in them the type and content of the perfume will sometimes be changed, with perfumes like that of the formula of Example 1 often being favored, and with the percentage sometimes being increased substantially, as up to 5%.

EXAMPLE 14

Air Freshener

| Component | Percent |
|---|---|
| *Propellant 12 | 47.5 |
| **Propellant 11 | 47.5 |
| Mineral oil | 2.0 |
| Perfume (of Example 2 formula) | 3.0 |
| | 100.0 |

*dichlorodifluoromethane
**trichloromonofluoromethane

The mineral oil and perfume are dissolved in the pressurized propellant mixture and such mixture is pressure filled into a dispensing container equipped with a spray nozzle designed for optimum spraying of the air freshener solution.

EXAMPLE 15

Powdered Odorant or Air Freshener

| Component | Percent |
|---|---|
| Clay, powdered | 99.0 |
| Perfume (of Example 1 formula) | 1.0 |
| | 100.0 |

EXAMPLE 16

Floor Wax

| Component | Percent |
|---|---|
| Montan based ester wax | 6.0 |
| Polyethylene wax | 4.0 |
| Non-oxidized microcrystalline wax | 5.0 |
| Tall oil fatty acids | 0.2 |
| Aqueous potassium hydroxide solution (43%) | 0.5 |
| N,N-diethylaminoethanol | 1.0 |
| Methyl carbitol | 1.0 |
| Perfume (of Example 1 formula) | 2.0 |
| Water | 80.3 |
| | 100.0 |

EXAMPLE 17

Aerosol Furniture Polish

| Component | Parts |
|---|---|
| Carnauba wax | 5.0 |
| Beeswax | 5.0 |
| Ceresin wax | 5.0 |
| Silicone oil (DC 200) | 5.0 |
| Stoddard solvent | 40.0 |
| Sodium soap (75:25 tallow:coco) | 2.0 |
| Water | 130.0 |

A wax-silicone concentrate is made by heating the Stoddard solvent to a temperature of about 52° C. and gradually adding to it the pre-melted waxes and silicone oil, with agitation. Concurrently, the soap is dissolved in the water at a temperature of about 90° C., after which the hot soap solution is admixed with the wax dispersion, under vigorous agitation. The mixture is then cooled rapidly to room temperature and 385 parts of water, 71 parts of naphtha and 20 parts of perfume (of Example 1 formula) are slowly added to it. 71 Parts of Propellant 12 are pressure loaded into dispensing containers after pre-loadings of the balance of the composition.

EXAMPLE 18

Shelf Paper

Rolls of shelf paper are sprayed on both sides thereof with perfume (of Example 2 formula) in volatile solvent, such as acetone or 95% ethanol, and are re-rolled after volatilization off of the solvent. The proportion of perfume is regulated to be 3%, although in some instances as little as 0.1% may be employed. The shelf paper has a long "shelf life" prior to use because loss of the perfume by volatilization is inhibited by the rolling of the paper. In a modification of this example the perfume is added to the paper pulp during the manufacturing process but care must be taken not to drive it off during drying operations.

EXAMPLE 19

Garbage Can Odorant

A 2% concentration of perfume (of Example 1 formula) in a sponge is made by injecting the liquid perfume into the interior of an open celled polyurethane foam, of flat cylindrical shape, which is inserted in an open holder affixed to the interior of the lid of a "step-on" kitchen waste container.

EXAMPLE 20

Insecticide

| Component | Percent |
|---|---|
| Boric acid | 97.0 |
| Perfume (of Example 2 formula) | 3.0 |
| | 100.0 |

In addition to the perfumes illustrated in Examples 1–4, a wide variety of other perfume types and formulas can be made, utilizing the described N-lower alkyl neoalkanamide perfuming materials. While properties of such materials will differ and their effects in various perfume formulas will be different, too, in general it may be said that the invented alkanamides will be satisfactorily volatile, of good substantivity so that they will be retained on surfaces to which they are applied, even from dilute liquid media, stable, so that they will not change substantially in fragrance when incorporated in various compositions and products, even when such are alkaline, persistent, so that they will last from a day to two weeks or more (being detectable after such times on a perfumer's blotter strip), and will desirably modify and often strengthen other perfuming materials, to produce a final perfume compound or perfumed product of modified or increased fragrance and increased strength of fragrance.

The various products described in Examples 5–20, while representative of those in which the N-lower alkyl neoalkanamides are considered to be useful, are only a few of the many compositions and articles of manufacture within the present invention, wherein the perfumes employed are improved by the presence therein of the described N-lower alkyl neoalkanamide(s). All of the described compositions are considered to be effective for the purposes indicated and additionally, they will often possess insect repellent properties, which are characteristic of the N-lower alkyl neoalkanamides, as set forth in the co-pending patent application entitled N-Alkyl Neoalkanamide Insect Repellents, referred to previously. In addition to the compositions recited in Examples 5–20, the described N-lower alkyl neoalkanamides can be satisfactorily employed in similar and other products, some of which are considered to be exceptionally severe tests for perfumes. For example, at perfume concentrations corresponding to 0.3% of N-methyl neodecanamide or 0.3% of N-ethyl neodecanamide in chlorinated powdered scouring cleansers, after two weeks of elevated temperature aging at 49° C. both neodecanamides exibit excellent odor and color stability. Similar excellent odor and color stability are also noted at neoalkanamide concentrations of 0.2% in a particulate phosphate-built synthetic organic detergent compositions and at 1% in toilet soap. The proportions of perfumes employed will normally be from 2 to 20 or 5 to 10 times the proportions of the N-lower alkyl neoalkanamides in the mentioned products. Generally, such products are not normally subjected to temperatures as high as 49° C. so the test is considered to be a severe one, especially when volatile materials are being tested, and therefore at room temperature the alkanamides are stable much longer.

This invention has been described with respect to various illustrations and embodiments thereof but is not to be limited to them because it is evident that one of skill in the art will be able to utilize substitutes and equivalents without departing from the invention.

What is claimed is:

1. An insect repellent liquid perfume which comprises an insect repelling and perfuming proportion, within the range of 0.1 to 98%, of N-lower alkyl neodecanamide wherein the lower alkyl is ethyl or methyl or a mixture thereof, and wherein the neodecanoic acid corresponding to the neodecanoyl moiety thereof is of the formula wherein the total number of carbon atoms in $R+R'+R''$ is 8, in which about 31% of such neodecanoic acid is of a structure wherein $R'$ and $R''$ are both methyl and R is hexyl, about 67% of the neodecanoic acid is of a structure wherein $R'$ is methyl, $R''$ i alkyl of a carbon atoms content greater than that of methyl and less than that of R, and R is of a carbon atoms content less than that of hexyl and greater than that of $R''$, and about 2% of the neodecanoic acid is of a structure wherein $R'$ and $R''$ are both of a carbon atoms content greater than that of methyl and less than that of R, and R is of a carbon atoms content less than that of hexyl and greater than those of $R'$ and $R''$, and a perfuming proportion of a perfuming component which is selected from the group consisting of essential oils, esters, ethers, aldehydes, alcohols, hydrocarbons, ketones and lactones.

2. An insect repellent perfume according to claim 1 which comprises 2 to 30% of the N-lower alkyl neodecanamide and at least 1% of each of such ester, aldehyde and alcohol perfume components.

3. An insect repellent liquid perfume according to claim 1 wherein the N-lower alkyl neodecanamide is N-ethyl neodecanamide, which is 5 to 15% of the perfume, and the balance of the perfume comprises 5 to 40% of citronellol, 5 to 30% of geraniol and 2 to 40% of phenylethyl alcohol.

4. An insect repellent liquid perfume according to claim 1 wherein the N-lower alkyl neodecanamide is one which is made by reacting a primary alkyl amine of 1 to 4 carbon atoms with a neodecanoic acid, which is made by reacting a corresponding alkene and carbon monoxide under high pressure and at elevated temperature in the presence of an aqueous acidic catalyst (Koch reaction).

5. An insect repellent perfume according to claim 4 which comprises 2 to 30% of the N-lower alkyl neodecanamide and at least 1% of each of such ester, aldehyde and alcohol perfume components.

6. A product or composition selected from the group consisting of particulate detergent compositions, toilet soaps, in bar or cake form, liquid detergents, detergent compositions for cleaning hard surfaces, shampoos for human hair, upholstery shampoos, rug shampoos, floor polishes, furniture polishes and scouring cleansers, which are perfumed with 0.1 to 10% of a perfume according to claim 1.

7. A product or composition according to claim 6 wherein the N-lower alkyl neodecanamide in the perfume is one which is made by reacting a primary alkyl amine of 1 to 4 carbon atoms with a neodecanoic acid (or its acid chloride) which is made by reacting a corresponding alkene and carbon monoxide under high pressure and at elevated temperature in the presence of an aqueous acidic catalyst (Koch reaction).

8. A method of perfuming a product or composition selected from the group consisting of particulate detergent compositions, toilet soaps, in bar or cake form, liquid detergents, detergent compositions for cleaning hard surfaces, shampoos for human hair, upholstery shampoos, rug shampoos, floor polishes, furniture polishes and scouring cleansers by applying to it or mixing with it an insect repellent liquid perfume of claim 1.

* * * * *